(12) United States Patent
Modlin

(10) Patent No.: US 6,258,326 B1
(45) Date of Patent: Jul. 10, 2001

(54) SAMPLE HOLDERS WITH REFERENCE FIDUCIALS

(75) Inventor: Douglas N. Modlin, Palo Alto, CA (US)

(73) Assignee: LJL BioSystems, Inc., Sunnyvale, CA (US)

( * ) Notice: Subject to any disclaimer, the term of this patent is extended or adjusted under 35 U.S.C. 154(b) by 0 days.

(21) Appl. No.: 09/156,318

(22) Filed: Sep. 18, 1998

Related U.S. Application Data

(60) Provisional application No. 60/089,848, filed on Jun. 19, 1998, provisional application No. 60/085,500, filed on May 14, 1998, and provisional application No. 60/059,640, filed on Sep. 20, 1997.

(51) Int. Cl.$^7$ .................................................... B01L 3/00
(52) U.S. Cl. ............................. 422/102; 422/99; 422/100; 422/104; 435/287; 435/297; 435/300; 435/301; 436/164; 436/165
(58) Field of Search ............................. 422/52, 63, 82.05, 422/82.08, 99, 102, 104; 436/43, 164, 165, 172; 356/244, 246; 435/297, 287, 293, 300, 301

(56) References Cited

U.S. PATENT DOCUMENTS

| | | |
|---|---|---|
| D. 303,149 | 8/1989 | Andersen . |
| 2,056,791 | 10/1936 | Logan . |
| 3,540,858 | 11/1970 | Rochte et al. . |
| 3,849,654 | 11/1974 | Malvin . |
| 4,011,451 | 3/1977 | Nelson . |
| 4,053,381 | 10/1977 | Hamblen et al. . |
| 4,067,653 | 1/1978 | Fletcher et al. . |
| 4,240,751 | 12/1980 | Linnecke et al. . |
| 4,245,052 | 1/1981 | Lund . |
| 4,292,273 | 9/1981 | Butz et al. . |
| 4,397,560 | 8/1983 | Andresen . |
| 4,545,958 | 10/1985 | Dopatka . |
| 4,591,550 | 5/1986 | Hafeman et al. . |
| 4,599,315 | 7/1986 | Terasaki et al. . |
| 4,622,208 | 11/1986 | Namba et al. . |

(List continued on next page.)

FOREIGN PATENT DOCUMENTS

| | | | |
|---|---|---|---|
| 0204109 | * 10/1986 | (EP) | ....................................... 422/99 |
| 0 542 422 A1 | 5/1993 | (EP) . | |
| 0 977 037 A1 | 2/2000 | (EP) . | |
| 1 003 020 A1 | 5/2000 | (EP) . | |
| 1 003 039 A1 | 5/2000 | (EP) . | |
| WO94/29024 | 12/1994 | (WO) . | |
| WO99/08233 | 2/1999 | (WO) . | |
| WO00/50877 | 8/2000 | (WO) . | |
| WO00/55372 | 9/2000 | (WO) . | |
| WO00/66269 | 11/2000 | (WO) . | |

OTHER PUBLICATIONS

PCR Reaction Vessels brochure, Corning Costar Corporation, Sep. 1996.

Miniprep 50 Mini Sample Processor brochure, Tecan AG, Jun. 1997.

Advanced Microplate Washers brochure, Tecan AG, Jul. 1997.

Genesis Series Robotic Sample Processors brochure, Tecan AG, Oct. 1997.

Genesis Robotic Microplate Processor brochure, Tecan AG, Nov. 1997.

(List continued on next page.)

*Primary Examiner*—T. Tung
*Assistant Examiner*—Dwayne K. Handy
(74) *Attorney, Agent, or Firm*—Kolisch, Hartwell, Dickinson, McCormack, & Heuser

(57) ABSTRACT

Reference fiducials for sample holders. The reference fiducials may be configured to provide information that facilitates sample handling and/or analysis. The sample holders may include microplates and biochips.

17 Claims, 4 Drawing Sheets

U.S. PATENT DOCUMENTS

| | | |
|---|---|---|
| 4,626,684 | 12/1986 | Landa . |
| 4,704,255 | 11/1987 | Jolley . |
| 4,704,353 | 11/1987 | Humphries et al. . |
| 4,730,921 | 3/1988 | Klein et al. . |
| 4,735,778 | 4/1988 | Maruyama et al. . |
| 4,738,825 | 4/1988 | Kelln et al. . |
| 4,741,619 | 5/1988 | Humphries et al. . |
| 4,762,420 | 8/1988 | Bowley . |
| 4,772,453 | 9/1988 | Linsenbee . |
| 4,801,804 | 1/1989 | Rosenthal . |
| 4,810,096 | 3/1989 | Russell et al. . |
| 4,873,633 | 10/1989 | Mezei et al. . |
| 4,883,579 | 11/1989 | Humphries et al. . |
| 4,892,409 | 1/1990 | Smith . |
| 4,894,347 | 1/1990 | Hillyard et al. . |
| 4,931,402 | 6/1990 | Abplanalp . |
| 4,936,682 | 6/1990 | Hoyt . |
| 4,948,442 | 8/1990 | Manns . |
| 4,968,148 | 11/1990 | Chow et al. . |
| 4,979,093 | 12/1990 | Laine et al. . |
| 4,979,821 | 12/1990 | Schutt et al. . |
| 5,020,995 | 6/1991 | Levy . |
| 5,047,215 | 9/1991 | Manns . |
| 5,084,246 | 1/1992 | Lyman et al. . |
| 5,086,002 | 2/1992 | Hillyard et al. . |
| 5,110,556 | 5/1992 | Lyman et al. . |
| 5,112,134 | 5/1992 | Chow et al. . |
| 5,169,601 | 12/1992 | Ohta et al. . |
| 5,198,670 | 3/1993 | VanCauter et al. . |
| 5,206,568 | 4/1993 | Bjornson et al. . |
| 5,208,161 | 5/1993 | Saunders et al. . |
| 5,216,488 | 6/1993 | Tuunanen et al. . |
| 5,225,164 | 7/1993 | Astle . |
| 5,262,128 | 11/1993 | Leighton et al. . |
| 5,273,718 | 12/1993 | Sköld et al. . |
| 5,275,951 | 1/1994 | Chow et al. . |
| 5,307,144 | 4/1994 | Hiroshi et al. . |
| 5,319,436 | 6/1994 | Manns et al. . |
| 5,340,747 | 8/1994 | Eden . |
| 5,341,215 | 8/1994 | Seher . |
| 5,349,436 | 9/1994 | Fisch . |
| 5,355,215 | 10/1994 | Schroeder et al. . |
| 5,384,093 | 1/1995 | Ootani et al. . |
| 5,401,465 | 3/1995 | Smethers et al. . |
| 5,436,718 | 7/1995 | Fernandes et al. . |
| 5,443,791 | 8/1995 | Cathcart et al. . |
| 5,449,921 | 9/1995 | Baba . |
| 5,457,527 | 10/1995 | Manns et al. . |
| 5,459,300 | 10/1995 | Kasman . |
| 5,487,872 | 1/1996 | Hafeman et al. . |
| 5,497,670 | 3/1996 | Carl . |
| 5,512,492 | 4/1996 | Herron et al. . |
| 5,516,490 | 5/1996 | Sanadi . |
| 5,527,684 | 6/1996 | Mabile et al. . |
| 5,531,697 | 7/1996 | Olsen et al. . |
| 5,540,889 | 7/1996 | Gordon et al. . |
| 5,542,012 | 7/1996 | Fernandes et al. . |
| 5,560,811 | 10/1996 | Briggs et al. . |
| 5,589,136 | 12/1996 | Northup et al. . |
| 5,589,350 | 12/1996 | Bochner . |
| 5,589,351 | 12/1996 | Harootunian . |
| 5,592,289 | 1/1997 | Norris . |
| 5,599,500 | 2/1997 | Jones . |
| 5,604,130 | 2/1997 | Warner et al. . |
| 5,620,894 | 4/1997 | Barger et al. . |
| 5,645,800 | 7/1997 | Masterson et al. . |
| 5,650,125 | 7/1997 | Bosanquet . |
| 5,663,545 | 9/1997 | Marquiss . |
| 5,670,113 | 9/1997 | Akong et al. . |
| 5,677,196 | 10/1997 | Herron et al. . |
| 5,679,310 | 10/1997 | Manns . |
| 5,736,410 | 4/1998 | Zarling et al. . |
| 5,738,825 | 4/1998 | Rudigier et al. . |
| 5,738,827 | 4/1998 | Marquiss . |
| 5,750,410 | 5/1998 | Dou et al. . |
| 5,756,050 | 5/1998 | Ershow et al. . |
| 5,756,304 | 5/1998 | Jovanovich . |
| 5,759,494 | 6/1998 | Szlosek . |
| 5,766,875 | 6/1998 | Hafeman et al. . |
| 5,770,151 | 6/1998 | Roach et al. . |
| 5,770,455 * | 6/1998 | Cargill et al. ................ 436/518 |
| 5,772,966 | 6/1998 | Maracas et al. . |
| 5,772,967 | 6/1998 | Wannlund et al. . |
| 5,798,035 * | 8/1998 | Kirk et al. ................ 205/335 |
| 5,798,085 * | 8/1998 | Seaton et al. ................ 422/65 |
| 5,800,778 | 9/1998 | Chen et al. . |
| 5,801,055 | 9/1998 | Henderson . |
| 5,811,256 | 9/1998 | Bryant . |
| 5,840,256 | 11/1998 | Demers et al. . |
| 5,842,582 | 12/1998 | DeStefano, Jr. . |
| 5,853,894 | 12/1998 | Brown . |
| 5,858,309 | 1/1999 | Mathus et al. . |
| 5,873,394 | 2/1999 | Meltzer . |
| 5,879,632 | 3/1999 | Demers . |
| 5,882,597 | 3/1999 | Astle . |
| 5,882,930 | 3/1999 | Baier . |
| 5,888,454 | 3/1999 | Leistner et al. . |
| 5,910,287 | 6/1999 | Cassin et al. . |
| 5,933,232 | 8/1999 | Atzler et al. . |
| 5,958,694 | 9/1999 | Nikiforov . |
| 5,961,926 | 10/1999 | Kolb et al. . |
| 5,989,835 | 11/1999 | Dunlay et al. . |
| 5,993,746 | 11/1999 | Priha et al. . |
| 6,018,388 | 1/2000 | Nawracala et al. . |
| 6,025,985 | 2/2000 | Leytes et al. . |
| 6,027,695 | 2/2000 | Oldenburg et al. . |
| 6,033,605 | 3/2000 | Szlosek . |
| 6,045,755 | 4/2000 | Lebl et al. . |
| 6,071,748 | 6/2000 | Modlin et al. . |

OTHER PUBLICATIONS

Miniprep 75 Robotic Sample Processor brochure, Tecan AG, Nov. 1997.

A Measure of Brilliance, TR717 Microplate Luminometer brochure, Tropix, Inc., 1997.

Advanced Microplate Detection Systems brochure, Tecan AG, Feb. 1998.

The SPECTRA Family brochure, Tecan AG, Feb. 1998.

Assist Plate Handling Device brochure, Labsystems, May 1998.

Genesis Assay Workstation brochure, Tecan AG, Jul. 1998.

Genesis Logistics Workstation brochure, Tecan AG, Jul. 1998.

Polarion brochure, Tecan AG, Aug. 1998.

A Catalog of Reagents, Microplates and Accessories of Life Science Research, Book 2, Packard BioScience Company, Dec. 1998.

CytoFluor Fluorescence Multi–Well Plate Reader brochure, PerSeptive Biosystems, 1998.

Setting the Standard, the HTS Compatibility Program brochure, Corning Incorporated, 1998.

Microplate Instrumentation Catalogue, Labsystems, 1998.

Luc–Screen brochure, Tropix, Inc., 1998.

Nunc Products 1998–1999 Catalog, Nalge Nunc International, 1998.

Advanced Microplate Washers, Tecan AG, Apr. 1999.

Everything's Great When it Sits on a Chip, Sinclair, *The Scientist*, vol. 13, No. 11, May 24, 1999.

CyBi™–Disk brochure, CyBio AG, Oct. 1999.
TWISTER™, Tecan's Automated Microplate Handler brochure, Tecan AG, Nov. 1999.
Magellan, Instrument Control and Data Analysis Software brochure, Tecan AG, Nov. 1999.
Handout Information, Tips and Tricks . . . Automated Liquid–Handling in the Microplate Format, CyBio AG, Nov. 1999.
Absorbance Readers brochure, Tecan AG, Dec. 1999.
ULTRA—The Solution for HTS and Assay Development brochure, Tecan Austria GmbH, Dec. 1999.
CyBi™–PlateSafe brochure, CyBio AG, May 2000.
CyBi™–Lumax 1,536 brochure, CyBio AG, May 2000.
CyBi™–Replicator brochure, CyBio AG, May 2000.
CyBi™–Well 2000 brochure, CyBio AG, May 2000.
Packard BioScience Company Introduces the Fusion™ Universal Microplate Analyzer press release, Packard BioScience Company, Jun. 29, 2000.
Fusion™, Universal Microplate Analyzer, Packard BioScience Company, Aug. 2000.
ProxiPlate internet description page, Packard BioScience Company, printed Sep. 17, 2000.
Approaching the 2 μL to 10 μL Range: 384 Well Small Volume vs. 1536 Well Plates poster, Greiner Labortechnik, Sep. 2000.
SPECTRAmax® GEMINI XS brochure, Molecular Devices Corp., Jun. 2000.
SPECTRAmax® PLUS$^{384}$ brochure, Molecular Devices Corp., Jun. 2000.
Labcyte: Research and Clinical Instruments for Life Sciences brochure, Arlena Research LLC, Aug. 1, 2000.
CyBi™–Screen–Machine: One System–Many Solutions brochure, CyBio AG, 2000.
Reacti–Bind™ Metal Chelate High Binding Capacity Plates flyer, Pierce Chemical Company, 2000.
Reacti–Bind™ Metal Chelate Plates flyer, Pierce Chemical Company, 2000.
Reacti–Bind™ NeutrAvidin™ High Binding Capacity (HBC) Coated Plates flyer, Pierce Chemical Company, 2000.
Reacti–Bind™ NeutrAvidin™ and Streptavidin Coated Plates flyer, Pierce Chemical Company, 2000.
Reacti–Bind™ Streptavidin High Binding Capacity (HBC) Coated Plates flyer, Pierce Chemical Company, 2000.
Nunc Life Science Discovery Products catalog, Nalge Nunc International Corporation, 2000.
FLIPR 384: Essential Technology for Drug Discovery brochure, Molecular Devices Corp., undated.
Acumen Explorer brochure, Acumen, undated.
FLUOstar Galaxy brochure, BMG Labtechnologies GmbH, undated.
LUMIstar Galaxy brochure, BMG Labtechnologies GmbH, undated.
NEPHELOstar brochure, BMG Labtechnologies GmbH, undated.
POLARstar Galaxy brochure, BMG Labtechnologies GmbH, undated.
POLARstar Galaxy flyer, BMG Labtechnologies GmbH, undated.
REMP 384 Tube Technology flyer, REMP (USA) Inc., undated.
REMP 96–Technology flyer, REMP (USA) Inc., undated.
High Throughput Screening brochure, Greiner America, Inc., undated.
PW 384 brochure, PanVera Corporation, undated.
Protein Kinase C (PKC) tech specs, PanVera Corporation, undated.
Falcon HTS FluoroBlok Inserts flyer, Becton Dickinson, undated.

* cited by examiner

SAMPLE HOLDERS WITH REFERENCE FIDUCIALS

CROSS-REFERENCES TO RELATED APPLICATIONS

This application is based upon and claims benefit under 35 U.S.C. § 119 of the following U.S. Provisional Patent Applications, each of which is incorporated herein by reference: Serial No. 60/059,640, filed Sep. 20, 1997; Serial No. 60/085,500, filed May 14, 1998, 1998; and Serial No. 60/089,848, filed Jun. 19, 1998.

This application incorporates by reference each of the following patent applications: U.S. patent application Ser. No. 09/062,472, filed Apr. 17, 1998; PCT patent application Ser. No. PCT/US98/14575, filed Jul. 15, 1998; U.S. patent application Ser. No. 09/118,141, filed Jul. 16, 1998; U.S. patent application Ser. No. 09/118,310, filed Jul. 16, 1998; U.S. patent application Ser. No. 09/118,341, filed Jul. 16, 1998; U.S. patent application Ser. No. 09/144,575, filed Aug. 31, 1998; U.S. patent application Ser. No. 09/144,578, filed Aug. 31, 1998; and U.S. patent application Ser. No. 09/146,081, filed Sep. 2, 1998.

This application also incorporates by reference each of the following U.S. Provisional Patent Applications: Serial No. 60/052,876, filed Jul. 16, 1997; Serial No. 60/059,639, filed Sep. 20, 1997; Serial No. 60/063,811, filed Oct. 31, 1997; Serial No. 60/072,499, filed Jan. 26, 1998; Serial No. 60/072,780, filed Jan. 27, 1998; Serial No. 60/075,414, filed Feb. 20, 1998; Serial No. 60/075,806, filed Feb. 24, 1998; Serial No. 60/082,253, filed Apr. 17, 1998; Serial No. 60/084,167, filed May 4, 1998; Serial No. 60/085,335, filed May 13, 1998; Serial No. 60/085,500, filed May 14, 1998; Serial No. 60/089,848, filed Jun. 19, 1998; Serial No. 60/094,275, filed Jul. 27, 1998; Serial No. 60/094,276, filed Jul. 27, 1998; and Serial No. 60/094,306, filed Jul. 27, 1998.

FIELD OF THE INVENTION

The invention relates to sample holders. More particularly, the invention relates to sample holders with reference fiducials configured to provide information that facilitates sample handling and/or analysis.

BACKGROUND OF THE INVENTION

Certain techniques in biology, chemistry, and medicine require processing large numbers of samples; such techniques include the high-throughput luminescence screening of candidate drug compounds, which may involve sequentially illuminating and monitoring the photoluminescence emission light transmitted from hundreds of thousands of samples. Processing large numbers of samples as in high-throughput screening may be facilitated by packaging samples together into high-density holders, such as "microplates" and "biochips," so that the samples may be analyzed together in an automated device.

Microplates are substantially rectilinear thermoplastic holders that include a plurality of sample wells for holding a plurality of samples. These sample wells typically are disposed in regular arrays, which may be of rectangular, hexagonal, or other geometry. Currently, the standard microplate includes 96 sample wells disposed in an 8×12 rectangular array on 9 millimeter (mm) centers.

Microplates may have other numbers of sample wells. FIG. 1 shows a stack of overlapping microplates having similar sizes and dissimilar numbers of sample wells. Microplate 30 has 96 sample wells. Microplate 32 has 384 sample wells. Microplate 34 has 1536 sample wells. Microplate 36 has 3456 sample wells. Microplate 38 has 9600 sample wells. The fluid volumes associated with these sample wells vary from several hundred microliters ($\mu$L) in the 96-well microplate to less than one microliter in the 9600-well microplate. The sample well dimensions associated with these sample well vary from several millimeters on a side in the 96-wells microplate to less than one millimeter on a side in the 9600-well microplate.

Biochips are substantially planar semiconductor devices used to hold and study biomolecules; a familiar example is a gene chip used to hold nucleic acids. Biochips may include many discrete sample positions, like microplates. Indeed, microplates begin to merge with biochips, such that the concept of a sample well begins to merge with the concept of a feature on a biochip, for microplates having very small sample wells.

Although microplates and biochips are of demonstrated utility in automated screening, they suffer from a number of shortcomings. Some shortcomings result from variations within the microplate and biochip. For example, microplates and biochips typically are made of plastic and may suffer distortions in the positions of sample wells and features due to shrinkage or expansion of the plastic. Other shortcomings result from inherent inaccuracies in the alignment mechanisms used to position microplates and biochips for sample analysis. Yet other shortcomings result from holder-to-holder variations in the microplate and biochip. For example, the overall size, sample well or feature size, construction material, and sample well or feature number and arrangement may vary, as shown for microplates in FIG. 1. To circumvent holder-to-holder variations, devices may limit sample analysis to only a single type of sample holder, such as a 96-well microplate.

If the positional error due to plastic deformation, inaccurate alignment mechanisms, or holder-to-holder variations in sample holders is a significant fraction of the feature size, then sample analysis will be adversely affected. For example, fluorescence signals may be decreased, and crosstalk from adjacent sites may be increased, especially when the array of sample wells or features is read with a step-and-repeat optical reader, which relies on moving to predetermined locations to perform fluorescence intensity measurements. These problems will be particular severe as the sample wells and features become smaller.

SUMMARY OF THE INVENTION

The present invention addresses these and other shortcomings by providing microplates having reference fiducials configured to provide information that facilitates sample handling and/or analysis.

The invention provides a sample holder for holding a plurality of samples for a preselected optical assay. Generally, the sample holder comprises (1) a frame, (2) a plurality of sample wells disposed in the frame, each sample well configured to hold a sample so that light transmitted from the sample during the preselected optical assay may be detected by a detection system, and (3) at least one reference fiducial that is not a sample well disposed in the frame, each reference fiducial configured to provide information that facilitates the preselected optical assay and to be interpretable by the same detection system that detects light transmitted from the sample.

The reference fiducial may be configured to provide a variety of information. For example, the reference fiducial may be configured to reduce cross-plate drift, or to facilitate alignment of the sample holder and the detection system. The reference fiducial also may be configured to provide information regarding microplate layout, including the manufacturer, overall size, sample well or feature size, construction material, and sample well or feature number and arrangement for the sample holder. The reference fiducial also may be configured to provide information regarding background luminescence from the microplate.

The invention also provides methods of performing assays involving sample holders, wherein reference fiducials provide information that facilitates conducting the assay.

DESCRIPTION OF THE INVENTION

Figure 1:
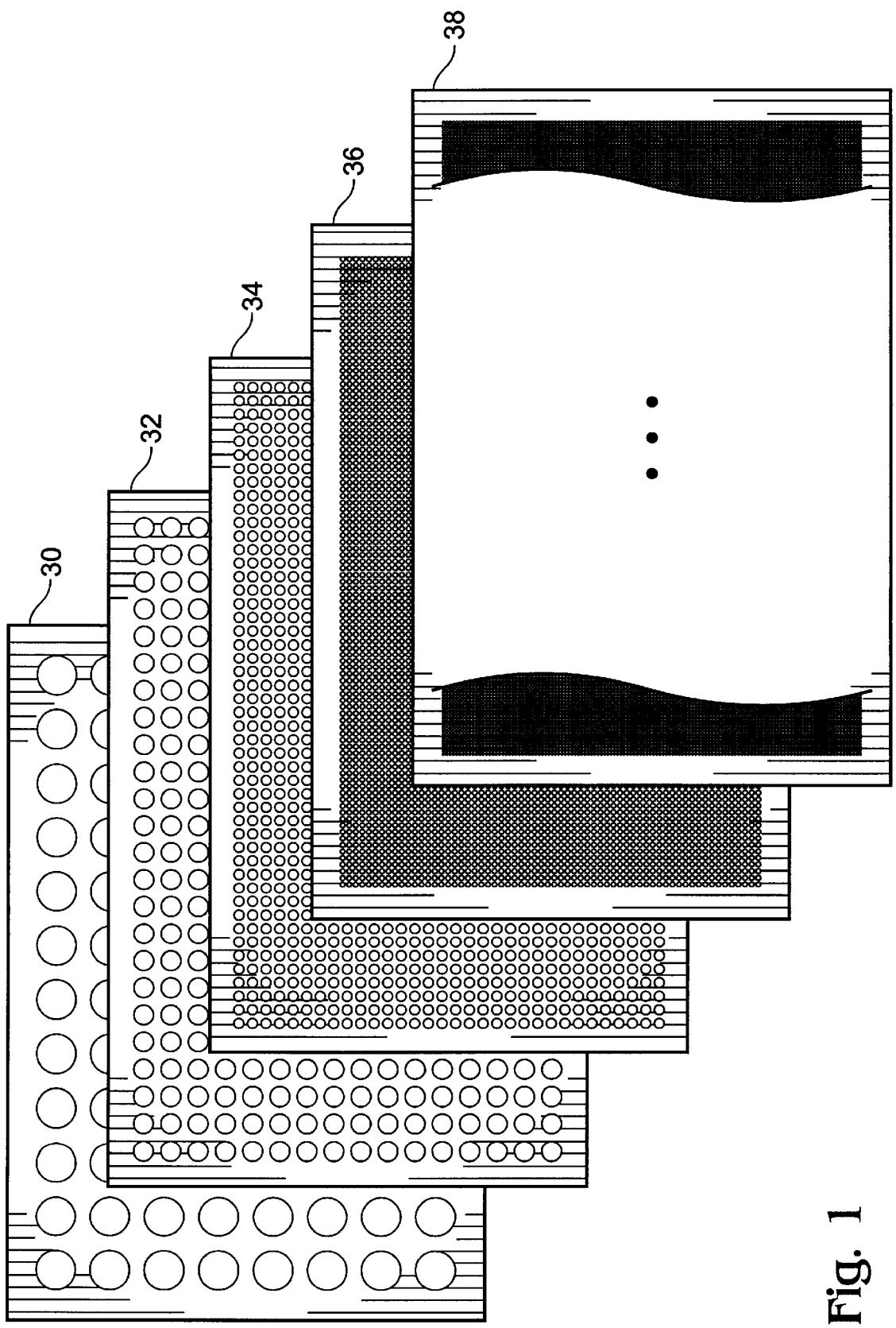
FIG. 1 is a top view of overlapping microplates showing variations in sample well density.
Figure 2:
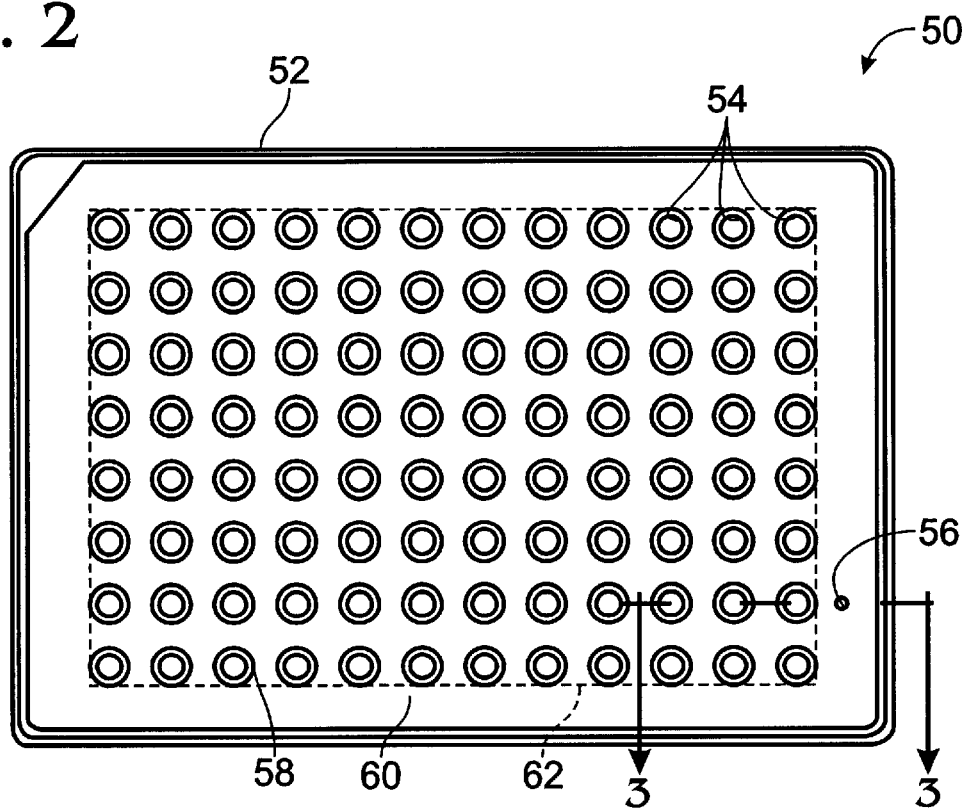
FIG. 2 is a top view of a 96-well microplate having a single reference fiducial.

FIG. 2 shows a top view of a 96-well microplate 50 constructed in accordance with the invention. Generally, the invention provides sample holders having reference fiducials configured to provide information that facilitates sample handling and/or analysis. Microplate 50 includes a frame 52, a plurality of sample wells 54 disposed in the frame, and a reference fiducial 56 disposed in the frame.

Frame 52 is the main structural component of microplate 50. Frame 52 is substantially rectangular and includes a sample well region 58 containing sample wells 54 and an edge region 60 forming a perimeter 62 around the sample well region. Reference fiducial 56 is disposed in edge region 60. Generally, reference fiducials may be disposed in either or both sample well region 58 and edge region 60. Frame 52 may be adapted to be easy to manufacture and to be minimally photoluminescent upon illumination. Frame 52 also may be constructed of a sturdy material, such as a thermoplastic, for repeated, rugged use.

Sample wells 54 are configured to hold a sample so that light transmitted from the sample during sample analysis may be detected by a detection system, such as the detection system in a high-throughput screening analyzer. Sample wells 54 are disposed as a substantially rectangular array. Generally, the sample wells are disposed at fixed positions, which may be ordered or unordered. Such ordered positions may include substantially regular arrays, which may be rectangular (as in FIG. 2), hexagonal, or of other shape.

Reference fiducial 56 is configured to provide information that facilitates sample handling and/or analysis and may be configured to be interpretable by the same detection system that detects light transmitted from the sample. The reference fiducial may encode information regarding microplate layout, including the dimensions of the sample wells alone, and the dimensions, composition, and manufacturer of the microplate as a whole. Such information may be used to reduce cross-plate drift and/or to facilitate alignment of the sample holder and a detection system, among other applications. Such information also may be used to set up the instrument for a particular preselected assay, if the information is determined before the assay.

Reference fiducial 56 also may be configured to provide information regarding background luminescence. For example, if reference fiducial 56 includes an aperture through the frame, information regarding background may be obtained by scanning the aperture and a portion of the frame adjacent the aperture with the detection system to determine their luminescence, and then comparing the luminescence of the aperture with the luminescence of the portion of the frame adjacent the aperture.

Figure 3:
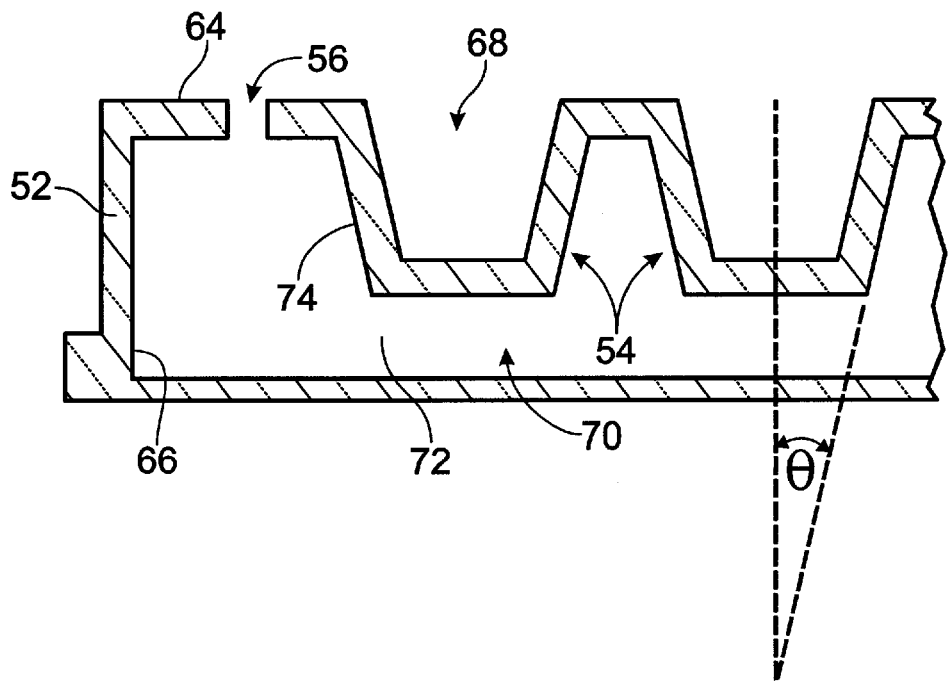
FIG. 3 is a cross-sectional view of the microplate of FIG. 2, taken generally along the line 3—3 in FIG. 2.

FIG. 3 shows a cross-sectional view of a portion of microplate 50, revealing frame 52, sample wells 54, and reference fiducial 56. Frame 52 has a top 64 and a bottom 66. Sample well 54 has an open, optically transparent end 68 directed toward top 64, and a closed, optically opaque end 70 directed toward bottom 66. Reference fiducial 56 is disposed on top 64, adjacent open end 68. Generally, reference fiducials may be disposed on either or both top 64 and bottom 66.

Sample wells 54 are substantially frusto-conical, with a substantially flat bottom wall 72 and substantially straight side walls 72 oriented at a cone angle θ. Frusto-conical-shaped sample wells conform most closely to the hourglass-shaped sensed volumes created by confocal optics detection systems, minimizing the amount of sample required for sample analysis. However, generally, sample wells may have a variety of shapes, including square, cylindrical, conical, and frusto-conical, among others.

Figure 4:
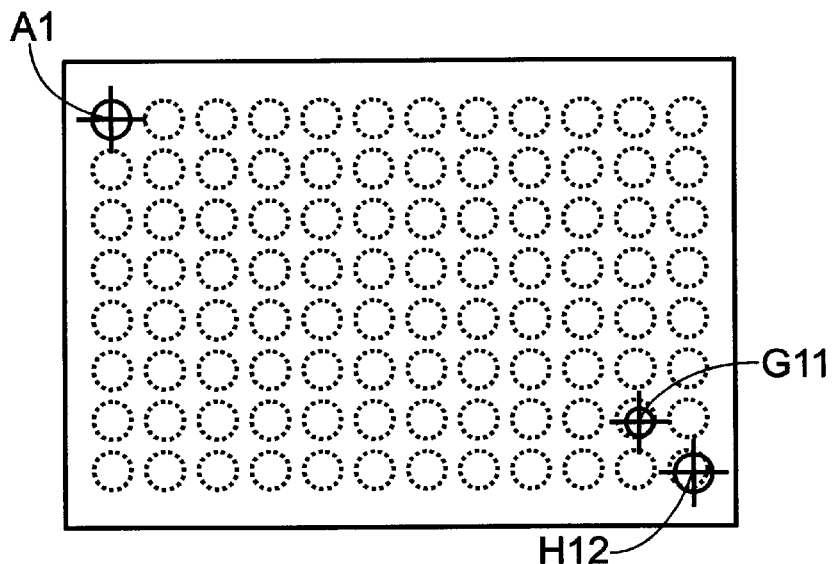
FIG. 4 is a schematic top view of a microplate showing the effects of cross-plate drift.

FIG. 4 shows a schematic top view of a 96-well microplate, showing how the geometry of the microplate affects the position of the sensed volume. A microplate analyzer may be configured automatically to find the location of each sample well in a given microplate, beginning with sample well A1. The analyzer may do this using stored parameters that describe the dimensions (e.g., microplate heights, interwell distances, etc.) of the particular microplate style. However, these microplate parameters are nominal and do not account for unit-to-unit or lot-to-lot variations in microplate geometry. If there is a slight variation in interwell distance, a calculated position may be off-center on some sample wells, even though it is perfectly on-center on sample well A1. This effect is termed cross-plate drift.

Cross-plate drift of fluorescence readings may increase as the instrument scans across the microplate, because variations will be compounded. Typically, drift will be worst at well H12, which is farthest from well A1. Such drift can be reduced by making the stage more accurate, by making the size of the sample holders more consistent, or by adjusting the analyzer to reduce the diameter of the observation region, thereby "putting it back" into the sample well. The lattermost approach is shown for well G11, relative to well H12.

Figure 5:
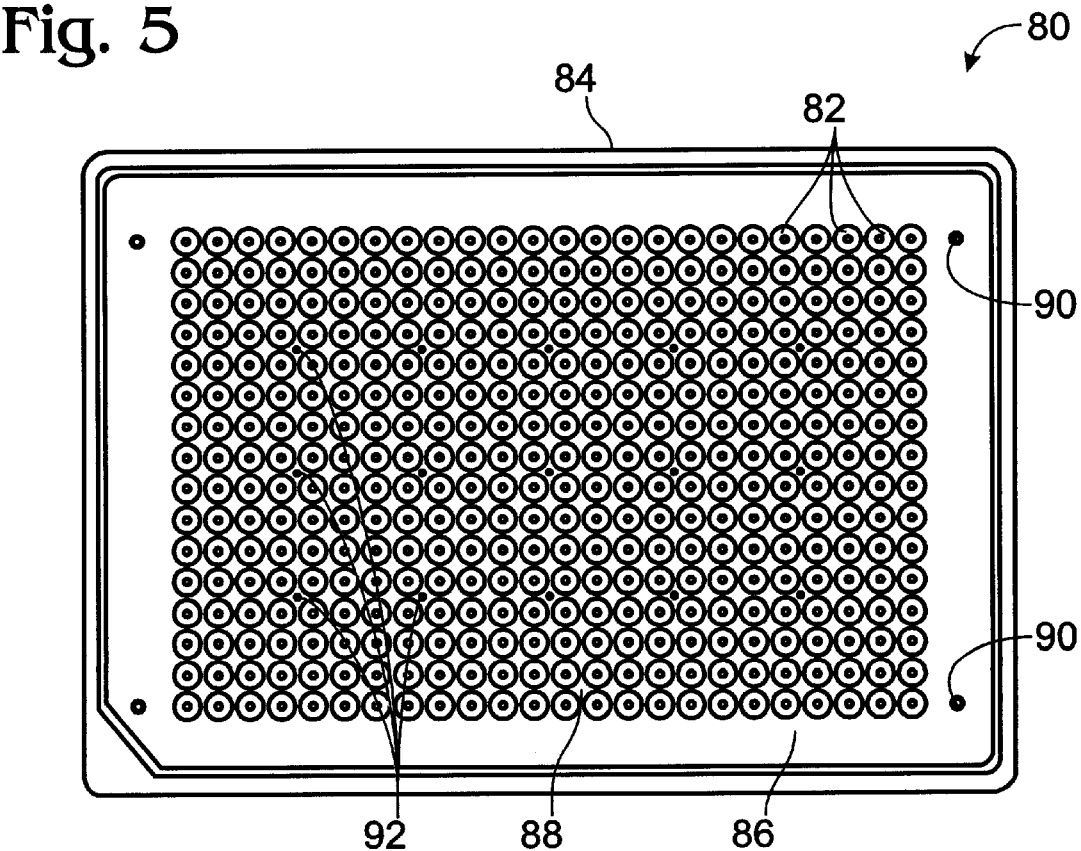
FIG. 5 is a top view of a 384-well microplate having a plurality of reference fiducials.

FIG. 5 shows a top view of a 384-well microplate 80 constructed in accordance with the invention, showing how reference fiducials may be used to reduce cross-plate drift. Microplate 80 includes sample wells 82 and a frame 84 having an edge region 86 and a sample well region 88. Microplate 80 also includes global reference fiducials 90 disposed in edge region 86 and local reference fiducials 92 disposed in sample well region 88.

Global and local reference fiducials may be employed as follows. First, an appropriate detection system locates the global reference fiducials. Second, the detection system locates the local reference fiducials for a given working area (defined as the sample wells adjacent the local reference fiducial), based on the positions of the global reference fiducials. When moving to new working areas, appropriate local reference features are located prior to processing. In principle, utilizing this technique, any desired level of positional accuracy may be obtained if enough reference fiducials are used to compensate for the distortion present in a microplate or chip substrate.

Figure 6:
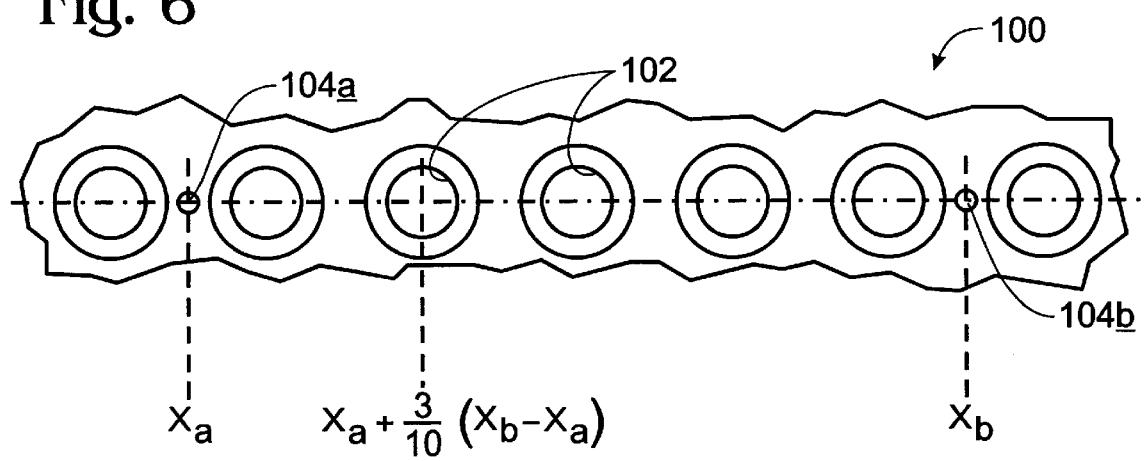
FIG. 6 is a top view of a portion of a microplate having a plurality of reference fiducials.

FIG. 6 shows a portion 100 of a microplate, showing how reference fiducials and an interpolation scheme may be employed to reduce cross-plate drift. Portion 100 includes seven sample wells 102 and two local reference fiducials 104a,b. First, the positions $X_a$ and $X_b$ of local reference fiducials 104a, b are determined, a task that may be facilitated using information from any global reference fiducials. Second, the separation X between the two local reference fiducials is determined by subtraction, $X = X_a - X_b$; a generalization of this formula (expressing the distance between two points) may be used for more complicated situations. Third, the separation is divided by five (the number of intervening sample wells). Finally, the position of each sample well is calculated by (1) adding multiples of one-fifth the separation to the position of the reference fiducial corresponding to the number of intervening sample wells and (2) adding an additional offset of one-tenth the separation to the position of the reference fiducial corresponding to the distance from a reference fiducial to the first sample well. Generally, reference fiducials may be used to determine the positions of sample wells and other reference fiducials using a variety of algorithms. These algorithms may involve interpolation, extrapolation, and/or other approaches.

Global and local reference fiducials play complementary roles. Overall variations in the sample holder generally may be determined more accurately using the global reference fiducials than the local reference fiducials, because global reference fiducials generally will be farther apart, so that errors in determining the positions of the reference fiducials will be less significant. Conversely, local variations in the sample holder generally may be determined more accurately using the local reference fiducials, because the relative positions of the global reference fiducials effectively average out local variations.

Reference fiducials may be employed not only to facilitate calculation of the positions of sample wells within the plane of the microplate, but also to facilitate calculation of positions perpendicular to the plane of the microplate. Such calculations allow the detection system to maintain an equal distance from the sample holder, independent of whether the sample holder is locally or globally warped.

Figure 7:
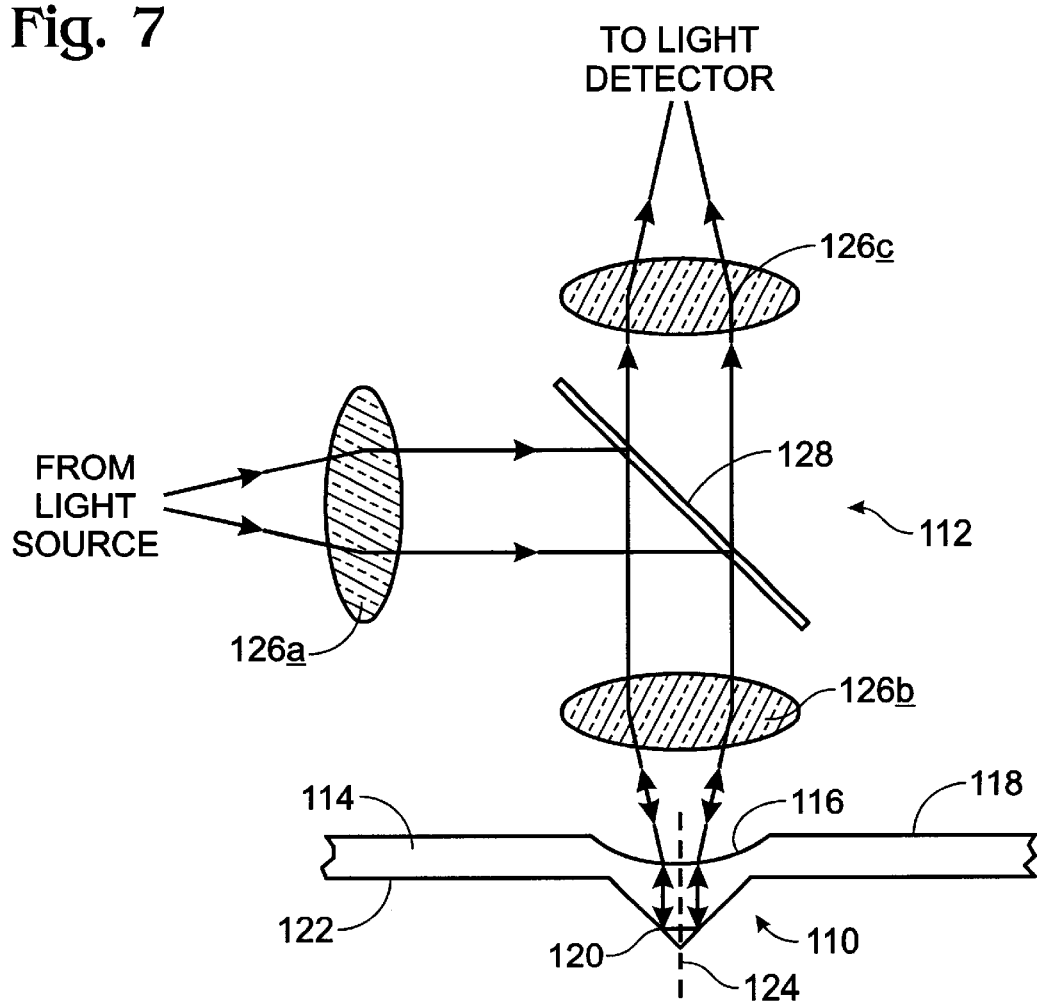
FIG. 7 is a partially schematic side elevation view showing a reflective reference fiducial in use.

FIG. 7 shows a partially schematic side elevation view of a reflective reference fiducial 110 and a detection system 112. Reflective reference fiducial 110 is molded into a microplate 114, and includes (1) a curved surface 116 near the top 118 of the microplate and (2) an angled surface 120 near the bottom 122 of the microplate. Reflective reference fiducial 110 has cylindrical symmetry about an axis 124 connecting curved surface 116 and angled surface 120. Detection system 112 includes (1) a light source, (2) first, second, and third lenses 126a–c, (3) a beamsplitter 128, and (4) a detector. Detection system 112 may be the same detection system used to detect light transmitted from a sample in microplate 114 during sample analysis.

Reflective reference fiducial 110 acts effectively as a small mirror, reflecting light transmitted by detection system 112 back into the detection system when the detection system and the reference fiducial are appropriately aligned. In this way, information encoded by the reference fiducial may be interpreted by the detection system. In use, light rays (denoted by arrows) from the light source pass through first lens 126a and are reflected off beamsplitter 128 through second lens 126b and onto curved surface 116. Curved surface 116 collimates the light rays and directs the collimated light rays onto angled surface 120. The collimated light rays are totally internally reflected by angled surface 120 and are directed back through second lens 126b, beamsplitter 128, and third lens 126c to the detector. Reflective reference fiducials may be formed of the same material used to form the frame and sample wells, deriving their reflective properties in part from total internal reflection; reflective reference fiducial 112 is an example. Reflective reference fiducials also may be formed of different materials, such as silver, deriving their reflective properties all or in part by ordinary reflection; a silvered spherical mirror is an example. The position of reflective reference fiducial 110 may be located in the x and y directions by scanning detection system 112 over the reference fiducial. Reflective reference fiducial 110 may function as a local and/or global reference fiducial.

Generally, the reference fiducials may include any reference feature associated with a sample holder like a microplate or a biochip that is configured to provide information that facilitates sample handling and/or analysis. The reference fiducial may include (1) an aperture through all or part of the frame, as in microplate 50 in FIGS. 2 and 3, (2) a reflective portion, as in microplate 114 in FIG. 7, and/or (3) other optical, acoustical, and/or mechanical features, among others. For example, a mechanical reference fiducial could be read using a linear voltage displacement transducer (LVDT), which measures displacement by creating a voltage proportional to the displacement.

Information may be encoded by the reference fiducial in various ways. Information may be encoded by size, shape, position, color, reflectivity, and/or other means. Information also may be encoded by the relative sizes, shapes, positions, colors, and/or reflectivities of a plurality of reference fiducials. Information also may be encoded by the ability of the reference fiducial to absorb, transmit, or reflect incident light; for example, if the detection system is capable of transmitting light to the reference fiducial.

The invention also provides methods for using reference fiducials. For example, the invention provides a method of reducing cross-plate drift during sample analysis. This method includes (1) providing a sample holder having a frame, a plurality of sample positions disposed in the frame, and at least two positional reference fiducials disposed in the frame, (2) determining the position of the positional reference fiducials, and (3) calculating the positions of the sample positions, based on the positions of the positional reference fiducials and the known relationship between the positions of the sample positions and the positions of the positional reference fiducials. The sample holder may include microplates, biochips, and other sample containers.

Although the invention has been disclosed in its preferred form, the specific embodiments thereof as disclosed and illustrated herein are not to be considered in a limiting sense, because numerous variations are possible. For example, although the invention was disclosed primarily in the context of microplates, it also applies to other sample holders, such as biochips. Applicants regard the subject matter of their invention to include all novel and non-obvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and non-obvious. Other combinations and subcombinations may be claimed through amendment of the present claims or presentation of new claims in this or a related application. Such claims, whether they are broader, narrower, or equal in scope to the original claims, also are regarded as included within the subject matter of applicants' invention.

We claim:

1. A microplate for holding a plurality of samples for a preselected optical assay, the microplate comprising:
    a frame;
    a plurality of sample wells disposed in the frame, each sample well configured to hold a sample, each sample well configured so that light transmitted from the sample during the preselected optical assay may be detected by a detection system; and
    at least one reference fiducial that is not a sample well disposed in the frame, each reference fiducial configured to identify the manufacturer of the microplate by the same detection system that detects light transmitted from the sample.

2. The microplate of claim 1, wherein the reference fiducial is configured to provide information regarding microplate layout.

3. The microplate of claim 1, wherein the reference fiducial is configured to provide information regarding background luminescence.

4. The microplate of claim 3, at least one reference fiducial including an aperture through the frame, wherein such reference fiducial may be used to provide information regarding background luminescence by scanning the aperture and a portion of the frame adjacent the aperture with the detection system to determine their luminescence, and comparing the luminescence of the aperture with the luminescence of the portion of the frame adjacent the aperture.

5. The microplate of claim 1, the detection system being capable of transmitting light to and from the reference fiducial, wherein the reference fiducial is configured to be interpretable by altering the amount of light transmitted, absorbed, or reflected by the reference fiducial.

6. The microplate of claim 1, wherein the reference fiducial includes an aperture.

7. The microplate of claim 6, wherein the information is encoded by the size of the aperture.

8. The microplate of claim 6, wherein the information is encoded by the position of the aperture.

9. The microplate of claim 1, wherein the reference fiducial provides information that facilitates the preselected assay if the information is determined before optical analysis.

10. The microplate of claim 1, the frame having a top and a bottom, the sample wells having an open end directed toward the top and a closed end directed toward the bottom, wherein the reference fiducial is disposed on the top.

11. The microplate of claim 1, each sample well having at least one optically transparent side, so that light may be transmitted during optical analysis between a sample in the sample well and the detection system through the optically transparent side, wherein the reference fiducial is positioned in a portion of the frame adjacent the transparent side.

12. The microplate of claim 1, wherein the reference fiducial is formed in the frame.

13. The microplate of claim 12, wherein the reference fiducial is configured to provide positional information that facilitates alignment of the microplate and the detection system.

14. A microplate for holding a plurality of samples for a preselected optical assay, the microplate comprising:
    a frame;
    a plurality of sample wells disposed in the frame, each sample well configured to hold a sample so that light transmitted from the sample during the preselected optical assay may be detected by a detection system; and
    a plurality of reference fiducials that are not sample wells, the reference fiducials being detectable by the detection system to compensate for effects of cross-plate drift.

15. The microplate of claim 14 further comprising a processor that uses light detection data from the fiducials to determine location of sample wells in the frame.

16. The microplate of claim 14, wherein the plurality of sample wells are divided into subsets according to preselected work areas, each work area having at least two reference fiducials that are used to determine the location of sample wells within the respective work area.

17. A microplate for holding a plurality of samples for a preselected optical assay, the microplate comprising:
    a frame;
    a plurality of sample wells disposed in the frame, each sample well configured to hold a sample, each sample well configured so that light transmitted from the sample during the preselected optical assay may be detected by a detection system;
    at least one reference fiducial that is not a sample well disposed in the frame, each reference fiducial configured to provide information that facilitates the preselected optical assay, each reference fiducial configured to be interpretable by the same detection system that detects light transmitted from the sample,
    wherein the reference fiducial includes at least one aperture through the frame, the reference fiducial being used to provide information regarding background luminescence by scanning the aperture and a portion of the frame adjacent the aperture with the detection system to determine their luminescence, and comparing the luminescence of the aperture with the luminescence of the portion of the frame adjacent the aperture.

* * * * *